(12) United States Patent
Sabaawy (10) Patent No.: US 9,770,470 B2
(45) Date of Patent: Sep. 26, 2017

(54) CLOSED SYSTEM SEPARATION OF ADHERENT BONE MARROW STEM CELLS FOR REGENERATIVE MEDICINE APPLICATIONS

(71) Applicant: Rutgers, The State University of New Jersey, New Brunswick, NJ (US)

(72) Inventor: Hatem Sabaawy, Neshanic Station, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/878,278

(22) Filed: Oct. 8, 2015

(65) Prior Publication Data

US 2016/0022739 A1  Jan. 28, 2016

Related U.S. Application Data

(62) Division of application No. 13/502,174, filed as application No. PCT/US2010/052883 on Oct. 15, 2010, now Pat. No. 9,169,464.

(Continued)

(51) Int. Cl.
*C12N 5/0775* (2010.01)
*A61K 35/28* (2015.01)
(Continued)

(52) U.S. Cl.
CPC .............. *A61K 35/28* (2013.01); *C12M 23/14* (2013.01); *C12M 25/06* (2013.01); *C12M 47/02* (2013.01);
(Continued)

(58) Field of Classification Search
None
See application file for complete search history.

(56) References Cited

U.S. PATENT DOCUMENTS 5,879,318 A   3/1999  Van Der Heiden et al.
5,965,436 A  10/1999  Thiede et al.
(Continued)

FOREIGN PATENT DOCUMENTS

JP   2008022822 A    2/2008
WO   2007083093 A1   7/2007

OTHER PUBLICATIONS

Lange, Claudia; et al; "Administered mesenchymal stem cells enhance recovery from ischemia/reperfusion-induced acute renal failure in rats" Kidney International, 68, 1613-1617, 2005.*

(Continued)

*Primary Examiner* — David Berke-Schlessel
(74) *Attorney, Agent, or Firm* — Fox Rothschild LLP (57) ABSTRACT

A method for isolating and processing bone marrow derived stem cells, including the steps of: (a) collecting a biological sample containing adherent bone marrow stem cells in a receptacle with interior walls coated with a cell-adherent substrate; (b) incubating the bone marrow cells on the adherent substrate so that a layer of adherent bone marrow stem cells adheres to the substrate; (c) washing any non-adherent cells from the substrate; and (d) collecting the bone marrow stem cell layer. Isolation kits and use of bone marrow cells harvested for cell therapies are also described.

14 Claims, 4 Drawing Sheets

Related U.S. Application Data (60) Provisional application No. 61/252,389, filed on Oct. 16, 2009.

(51) Int. Cl.
*C12M 1/00* (2006.01)
*C12M 1/12* (2006.01)
*C12N 5/077* (2010.01)
*C12N 5/071* (2010.01)
*A61K 35/12* (2015.01)

(52) U.S. Cl.
CPC ......... *C12N 5/0663* (2013.01); *C12N 5/0669* (2013.01); *C12N 5/0672* (2013.01); *A61K 2035/124* (2013.01); *C12N 2533/32* (2013.01)

(56) References Cited

U.S. PATENT DOCUMENTS

| | | | |
|---|---|---|---|
| 6,059,968 | A | 5/2000 | Wolf, Jr. |
| 7,795,024 | B2 | 9/2010 | Madlambayan et al. |
| 2006/0286669 | A1* | 12/2006 | Song ................... C12N 5/0607 435/325 |
| 2007/0032882 | A1 | 2/2007 | Lodhi et al. |
| 2007/0082397 | A1 | 4/2007 | Hasson et al. |
| 2007/0154877 | A1 | 7/2007 | Schuler et al. |
| 2007/0259394 | A1 | 11/2007 | Kanome et al. |

OTHER PUBLICATIONS

Yoo, Jung U; et al; "The Chondrogenic Potential of Human Bone-Marrow-Derived Mesenchymal Progenitor Cells" The Journal of Bone and Joint Surgery, 80-A, 1745-1757, 1998.*

Kern, Susanne; et al; "Comparative Analysis of Mesenchymal Stem Cells from Bone Marrow, Umbilical Cord Blood, or Adipose Tissue" Stem Cells, 24, 1294-1301, 2006.*

AU, Dissertation: "Molecular Substrate Design for the Selective Adhesion, Proliferation, and Differentiation of Marrow Connective Tissue Progentors", Massachusetts Institute of Technology, Oct. 27, 2005, pp. 1-167.

Bieback, et al.: "Clinical Protocols for the Isolation and Expansion of Mesenchymal Stromal Cells", Transfusion Medicine and Hemotherapy, 2008, vol. 35, pp. 286,294.

Gurevich, et al. "Fibrin Microbeads for Isolating and Growing Bone Marrow-Derived Progenitor Cells Capable of Forming Bone Tissue", Tissue Engineering, 2002, vol. 8, pp. 661-672.

Kinya Ito et al.: "A Novel Method to isolate Mesenchymal Stem Cells from Bone Marrow in a Closed System Using a Device Made by Nonwoven Fabric", Tissue Engineering, Part C, Methods Feb. 2010, vol. 16, No. 1, Jul. 6, 2009, pp. 81-91.

Lachmann et al: "Tailor-Made Surface Coatings for Cell Cultivation in a Closed Plastic Bag System", 19th International Symposium on Plasma Chemistry Bochum, Germany, Jul. 26-31, 2009, Jul. 26, 2009, pp. 1-4.

Sotiropoulou, et al: "Characterization of the Optimal Culture Conditions for Clinical Scale Production of Human Mesenchymal Stem Cells", Stem Cells, 2006, vol. 24, pp. 462-471.

Warkentin, et al.: "Transplant of Major ABO-Incompatible Bone Marrow Depleted Red Cells by Hydroxyethyl Starch", Vox Sanguinis, 1985, vol. 48, pp. 89-104.

Written Opinion of the International Searching Authority and International Search Report mailed Dec. 21, 2010 or Application No. PCT/US2010/052883.

Information about Other Patent Applications, see section 6 of the accompanying Information Disclosure Statement Letter, which concerns Other Patent Application.

Bieback et al: "Critical Parameters for the Isolation of Mesenchymal Stem Cells from Umbilical Cord Blood", Stem Cells, 2004, vol. 22, pp. 625-634.

\* cited by examiner

CLOSED SYSTEM SEPARATION OF ADHERENT BONE MARROW STEM CELLS FOR REGENERATIVE MEDICINE APPLICATIONS

CROSS REFERENCE TO RELATED APPLICATION

This application is a Divisional of U.S. application Ser. No. 13/502,174, filed Apr. 16, 2012 which is the U.S. National Phase of International Patent Application Serial No. PCT/US10/52883, filed Oct. 15, 2010, which claims priority under 35 U.S.C. §119(e) to U.S. Provisional Patent Application No. 61/252,389 filed on Oct. 16, 2009. The contents of the foregoing applications are incorporated herein by reference in their entireties.

FIELD OF THE INVENTION

This invention is related to a novel method for isolation of bone marrow-derived stem cells, an isolation kit useful for the novel isolation method, and the use of the bone marrow cells harvested by the novel isolation method for cell therapies.

BACKGROUND OF THE INVENTION

Stem cell research has become an important field of study for molecular, cellular, and clinical biology as well as pharmaco-toxicology, because stem cells have a strong proliferative and unlimited self-renewal potential and are multipotent. Evidence has suggested that progenitor cells outside the central nervous system, bone marrow cells in particular, may have the ability to generate either neurons or glia in vivo. Toma et al., *Nat. Cell Biol.* 3:778-783 (2001); Mezey, E. et al., *Science* 290:1779-1782 (2000); Brazleton, T. R. et al., *Science* 290:1775-1779 (2000); and Eglitis, M. A. et al., *Proc Natl. Acad. Sci.* 94:4080-4085 (1997).

Adult bone marrow stromal cells are rare heterogeneous cells including multipotent mesenchymal stromal cells (MSC), adventitial reticular cells, vascular pericytes, and bone-lining cells (Jones, E. & McGonagle, D. *Rheumatology (Oxford)* 47, 126-31 (2008); Prockop, D. J. *Mol. Ther.* 17, 939-46 (2009)). These cells are capable of self-renewal, and able to transcribe genes for multiple embryonic germ layers. (Labat, M. L. et al., *Biomed. Pharmacother.* 54, 146-62 (2000); Woodbury, D. et al., *J. Neurosci. Res.* 69, 908-17 (2002)). In vivo as well as in vitro studies have confirmed the differentiation of adult bone marrow stem cells into muscle cells, adipocytes, cardiomyocytes, neuroectodermal cells, osteoblasts, chondroblasts, and so on. Recently, it was shown that, under appropriate culture conditions, adult bone marrow stem cells may also differentiate into hepatocyte-like cells, which demonstrates the high potential of adult bone marrow stem cells being used as an unlimited source of hepatocytes for pharmaco-toxicological research and testing. Snykers, S. et al., *Methods in Molecular Biology* (2006).

However, the identification and isolation of stem cells are challenging, mainly for two reasons. First, stem cells are rare. In bone marrow, for example, where hematopoiesis occurs, there is only one stem cell for every several billion bone marrow cells. Vogel, G. *Science*, 287, 1418-1419 (2000). Second, it is difficult to identify molecular markers which are unique to stem cells, especially because primitive stem cells may be in a quiescent state and thus may express few molecular markers. Gage, F. H. *Science*, 287, 1433-1488 (2000).

Some isolation methods of bone marrow stem cells have been reported recently. For example, density-gradient centrifugation is used to isolate murine hematopoietic stem cells on the basis of functional characteristics such as the ability of stem cells to home to bone marrow and aldehyde dehydrogenase (ALDH) activity. An essential component of this method is the separation of whole bone marrow into small-sized cells by counter-flow elutriation instead of the normal elutriation. Juopperi, T. A. et al., *Exp Hematol.* 2007 February; 35(2):335-41. Recently, a new method for isolation of bone marrow derived liver stem cells (BDLSC) was reported, which involves using a cholestatic serum as the selecting culture system to purify BDLSC directly from bone marrow cells. Cai, Y. F. et al. *World J. Gastroenterol* 2009; 15(13): 1630-1635. The results suggest that BDLSCs can be purified and passaged. All references cited herein are hereby incorporated by reference in their entirety.

Despite the limited success reported, isolation of bone marrow stem cells remains to be challenging; therefore, development of new methods for isolating bone marrow stem cells is much needed for the fast growing stem cell research and development, and in particular, for the applications of stem cells in cell therapies.

U.S. Pat. No. 6,733,433 discloses a blood separation method particularly for concentrating hematopoietic stem cells. U.S. Pat. No. 5,879,318 similarly discloses methods and closed system for isolating and processing umbilical cord blood. Finally, U.S. Pat. No. 7,279,331 discloses similar methods of isolating cord matrix mesenchymal stem cells from cord fragments. However, none of the three methods allow for the separation of adherent bone marrow or cord blood cells in the same vessel or bag.

SUMMARY OF THE INVENTION

The present invention fulfills the foregoing need by providing a novel method for isolating and processing bone marrow derived stem cells. The invention also includes a novel kit useful for the isolation of stem cells and the use of the bone marrow cells thus harvested in cell therapies.

In a first aspect, the present disclosure provides a method for isolating and processing bone marrow derived stem cells in the same vessel, the method comprising the steps of:

(a) collecting a biological sample containing adherent bone marrow stem cells in a receptacle with interior walls coated with a cell-adherent substrate;

(b) incubating the bone marrow cells on the adherent substrate so that a layer of adherent bone marrow stem cells adheres to the substrate;

(c) washing any non-adherent cells from adherent substrate; and (d) collecting the cell layer containing adherent bone marrow stem cells.

In a second aspect, the present disclosure provides a method of regenerative therapy by administering bone marrow stem cells to tissues from which regeneration can be elicited by the stem cells, wherein the improvement administers stem cells collected by the method according to the first aspect of the present disclosure as described above.

In a third aspect, the present disclosure provides a stem cell isolation kit, containing the following components:

(a) a first cell collection bag containing a predetermined quantity of a plasma blood volume expander;

(b) a second cell collection bag with an interior surface coated with a cell-adherent surface layer and containing a predetermined quantity of growth medium; and (c) sterile connection means for transferring the contents of the first bag to the second bag.

The second cell collection bag disclosed herein represents a new therapeutic strategy for use of autologous (patient's own) adult bone marrow stem cells for regenerative therapy in a simple process that can be preformed as an outpatient procedure. As an illustrated example, the present inventors have utilized the adhesive property to select bone marrow cells for autologous cell therapy by intrathecal injections in spinal cord injury (SCI). Direct intrathecal injection permits delivery of enough stem cells into the brain and spinal cord to elicit neuronal and astrocytic differentiation.

In another aspect, the disclosed embodiments are designed to meet the U.S. Food and Drug Administration (FDA)'s requirement for use of biological therapies. This strategy has wide applications, which may include all elements of regeneration and repair of human diseases including neurodegenerative, traumatic, and organ failure disorders. Thus, the advantages of using the stem cell-bag therapeutic strategy disclosed herein invention include, inter alia: (1) it is safe because it utilizes patient's own cells; (2) it can be tolerated without needing immune suppression or conditioning; (3) it is effective, as it has been successfully used to treat the spinal cord injury (SCI); (4) it is minimally invasive through local injection; (5) it has broad applications, because adult stem cells can be used for multiple regenerative potentials in essentially all tissues; (6) it is more ethically acceptable than the use of fetal stem cells for the same purposes; and (7) it complies with the FDA's current good manufacture practice (GMP) and thus is bedside ready and suitable for clinical trials.

DESCRIPTION OF THE PREFERRED EMBODIMENTS

The present invention is based on the discovery that adult bone marrow stem cells display similar surface phenotypes but have a selective adherence to certain tissue culturing polymeric substrates that allows separation of stem cells with different potentials.

In a first aspect, the present disclosure provides a method for isolating and processing bone marrow derived stem cells from a biological sample.

In a first embodiment of the first aspect, the present disclosure provides a method for isolating and processing bone marrow derived stem cells, the method including the steps of:

(a) collecting a biological sample containing adherent bone marrow stem cells in a receptacle with interior walls coated with a cell-adherent substrate;

(b) incubating the bone marrow stem cells on the cell-adherent substrate so that a layer of the bone marrow stem cells adheres to said substrate;

(c) washing any non-adherent cells from the adherent substrate; and (d) collecting the adherent bone marrow stem cell layer.

In a second embodiment of the first aspect, the present disclosure provides a method for isolating and processing bone marrow derived stem cells in which the biological sample contains red blood cells and the step of collecting the biological sample described in the first embodiment further include the step of: receiving from a subject a biological sample containing red blood cells and bone marrow stem cells and separating the red blood cells from the biological sample before the bone marrow stem cells are incubated.

In a third embodiment of the first aspect, the present disclosure provides a method for isolating and processing bone marrow derived stem cells, including the steps described in the first embodiment, wherein the biological sample is autologous.

In a fourth embodiment of the first aspect, the present disclosure provides a method for isolating and processing bone marrow derived stem cells, including the steps described in the first embodiment, wherein the biological sample is umbilical cord blood or bone marrow aspirates.

In a fifth embodiment of the first aspect, the present disclosure provides a method for isolating and processing bone marrow derived stem cells, including the steps described in the first embodiment, wherein the cell-adherent substrate is a polymeric substrate coated with a cell-adherent biopolymer, polypeptide, protein or polysaccharide.

In a sixth embodiment of the first aspect, the present disclosure provides a method for isolating and processing bone marrow derived stem cells, including the steps described in the fourth embodiment, wherein the polymer substrate is corona discharge treated prior to coating with the cell-adherent biopolymer, polypeptide, protein or polysaccharide.

In a seventh embodiment of the first aspect, the present disclosure provides a method for isolating and processing bone marrow derived stem cells, including the steps described in the fourth embodiment, wherein the cell-adherent substrate coating is a coating of one or more basement membrane proteins.

In an eighth embodiment of the first aspect, the present disclosure provides a method for isolating and processing bone marrow derived stem cells, including the steps described in the sixth embodiment, wherein the basement membrane proteins are selected from fibronectin, collagen, laminin, keratin, fibrin and fibrinogen.

In a ninth embodiment of the first aspect, the present disclosure provides a method for isolating and processing bone marrow derived stem cells, including the steps described in the fourth embodiment, wherein the substrate is coated with gelatin.

In a tenth embodiment of the first aspect, the present disclosure provides a method for isolating and processing bone marrow derived stem cells, including the steps described in the fourth embodiment, wherein the cell-adherent substrate coating is a coating of one or more polysaccharides selected from hyaluronic acid, heparin sulfate, chondroitin sulfate and agarose.

In an eleventh embodiment of the first aspect, the present disclosure provides a method for isolating and processing bone marrow derived stem cells, including the steps described in the fourth embodiment, wherein the substrate is coated with poly-L-lysine or poly-D-lysine.

In a twelfth embodiment of the first aspect, the present disclosure provides a method for isolating and processing bone marrow derived stem cells, including the steps described in the first embodiment, wherein the red blood cells are separated by mixing the sample with a growth medium and diluting the mixture with an amount of plasma blood volume expander effective to separate the red blood cells therefrom.

In a thirteenth embodiment of the first aspect, the present disclosure provides a method for isolating and processing bone marrow derived stem cells, including the steps described in the eleventh embodiment, wherein the sample is mixed about 1:1 with ex vivo 10 growth medium.

In a fourteenth embodiment of the first aspect, the present disclosure provides a method for isolating and processing bone marrow derived stem cells, including the steps described in the eleventh embodiment, wherein the sample mixed with growth medium is further mixed with the plasma blood volume expander in a first cell collection bag.

In a fifteenth embodiment of the first aspect, the present disclosure provides a method for isolating and processing bone marrow derived stem cells, the method including the steps described in the first embodiment, wherein the step of contacting the cells with a cell-adherent substrate includes transferring the cells to a second cell collection bag, the interior surface of which is coated with a cell-adherent biopolymer, polypeptide, protein or polysaccharide.

In a sixteenth embodiment of the first aspect, the present disclosure provides a method for isolating and processing bone marrow derived stem cells, including the steps described in the fourteenth embodiment, wherein the cells are mixed with a growth medium in said second bag.

In a seventeenth embodiment of the first aspect, the present disclosure provides a method for isolating and processing bone marrow derived stem cells, including the steps described in the first embodiment, wherein the cells are incubated on the substrate between about two hours and about five days. In a more specific embodiment, the cells are incubated between about three hours and about 72 hours.

In an eighteenth embodiment of the first aspect, the present disclosure provides a method for isolating and processing bone marrow derived stem cells, the method including the steps described in the first embodiment, wherein non-adherent cells are washed from the substrate by replacing said growth medium.

In a nineteenth embodiment of the first aspect, the present disclosure provides a method for isolating and processing bone marrow derived stem cells, including the steps described in the seventeenth embodiment, wherein the replacing step is performed more than once.

In a twentieth embodiment of the first aspect, the present disclosure provides a method for isolating and processing bone marrow derived stem cells, including the steps described in the first embodiment, wherein said bone marrow stem cells are collected by incubating the adherent cell layer with a cell detachment solution.

In a twenty-first embodiment of the first aspect, the present disclosure provides a method for isolating and processing bone marrow derived stem cells, including the steps described in the first embodiment and further including the step of suspending the collected bone marrow stem cells in a pharmaceutically acceptable saline solution.

In a twenty-second embodiment of the first aspect, the present disclosure provides a method for isolating and processing bone marrow derived stem cells, including the steps described in the first embodiment and further including the step of checking the collected bone marrow stem cells for at least one of cell phenotype, viability, and sterility.

In a second aspect, the present disclosure provides a method of regenerative therapy, in which the method administers stem cells to tissues from which regeneration can be elicited by the stem cells, wherein the improvement administers stem cells collected by the method described in any of the embodiments described above in the first aspect of the present disclosure.

In a third aspect, the present disclosure provides a stem cell isolation kit.

In a first embodiment of the third aspect, the present disclosure provides a stem cell isolation kit, containing:
(a) a first cell collection bag containing a predetermined quantity of a plasma blood volume expander;
(b) a second cell collection bag having an interior surface coated with a cell-adherent surface layer and containing a predetermined quantity of growth medium; and
(c) sterile connection means for transferring the contents of the first bag to the second bag.

In a second embodiment of the third aspect, the present disclosure provides a stem cell isolation kit described in the first embodiment above, further containing a container with a predetermined amount of growth medium for receiving a biological sample containing red blood cells and bone marrow stem cells.

In a third embodiment of the third aspect, the present disclosure provides a stem cell isolation kit described in the second embodiment above, wherein the growth medium in the container is X-vivo.

In a fourth embodiment of the third aspect, the present disclosure provides a stem cell isolation kit described in the first embodiment above, further containing one or more containers of replacement growth media for the second container.

In a fifth embodiment of the third aspect, the present disclosure provides a stem cell isolation kit described in the first embodiment above, further including a container of cell detachment solution.

In a sixth embodiment of the third aspect, the present disclosure provides a stem cell isolation kit described in the first embodiment above, further including aspirating means for collecting bone marrow aspirates.

In a seventh embodiment of the third aspect, the present disclosure provides a stem cell isolation kit described in the first embodiment above, wherein the interior surface of the collection bag is corona discharge treated before being coated with the cell-adherent surface layer.

In an eighth embodiment of the third aspect, the present disclosure provides a stem cell isolation kit described in the first embodiment above, wherein the cell-adherent surface layer includes a natural or synthetic cell-adherent biopolymer, polypeptide, protein or polysaccharide.

In a ninth embodiment of the third aspect, the present disclosure provides a stem cell isolation kit described in the eighth embodiment above, wherein the cell-adherent surface layer includes one or more basement membrane proteins.

In a tenth embodiment of the third aspect, the present disclosure provides a stem cell isolation kit described in the ninth embodiment above, wherein the basement membrane proteins are selected from fibronectin, collagen, laminin, keratin, fibrin and fibrinogen.

In an eleventh embodiment of the third aspect, the present disclosure provides a stem cell isolation kit described in the eighth embodiment above, wherein the cell-adherent surface layer includes one or more polysaccharides selected from hyaluronic acid, heparin sulfate, chondroitin sulfate and agarose.

In a twelfth embodiment of the third aspect, the present disclosure provides a stem cell isolation kit described in the eighth embodiment above, wherein the cell-adherent surface layer includes poly-L-lysine or poly-D-lysine.

In yet another aspect, the present invention encompasses the use of the bone marrow derived progenitor stem cells to treat any conditions or disorders that respond to such treatment.

The present invention may be used for isolation and processing of any tissue-regenerating stem cells, which may include stem cells from, by way of example, mammalian bone marrow, adipose tissue, or any suitable fetal tissue. Preferably, the stem cells are obtained from the bone marrow of a non-fetal mammal, and most preferably from a human.

In a preferred embodiment of the present invention, a mass of cells may be harvested or otherwise obtained from an appropriate source. The mass of cells may thereafter be grown in a culture, and may be further sub-cultured where desirable, to generate further masses of cells. Such separation may be repeated any desirable number of times to generate a clinically useful amount of stem cells.

A preferred embodiment for carrying out the present invention is to isolate the BM progenitor stem cells under the FDA's current Good Manufacturing Practice (GMP) conditions.

The bone marrow progenitor stem cells isolated according to the present invention possess a host of potential clinical and therapeutic applications, as well as applications in medical research. Two possible therapeutic mechanisms include: (1) using the cells as a delivery vehicle for gene products by taking advantage of their ability to migrate after transplantation, and (2) using the cells to repair damaged tissues, for example, regenerating neurons, thereby restoring or enhancing tissue function.

The cells harvested in accordance with the method of the present invention can in principle be used for any stem cell therapy, regardless of the diseases or conditions or the sources of the stem cells. An illustrative example of the treatment of such diseases or disorders includes a cell therapy strategy for treatment of spinal cord injury (SCI), in which autologous minimally manipulated adherent BM-derived cells (ABMC) are transplanted by intrathecal injections.

The advantages of autologous transplantation using adult stem cells include, but not limited to, a superior safety profile as compared to the use of fetal cells. Because the method disclosed herein retains the in vivo features of the stem cells, through research and development for tissue repair to augment or replace organ transplant, the method has potential for the growing therapeutic applications of isolated adult stem cells. This technology would allow the use of scaffolds to regenerate three-dimensional structures and tissues for repair and replacement of most tissues.

DEFINITIONS

The term "basement membrane," as used herein, refers to a thin sheet of fibers that underlies the epithelium, which lines the cavities and surfaces of organs, or the endothelium, which lines the interior surface of blood vessels.

The term "basement membrane protein," as used herein, refers to proteins expressed on tissue basement membranes, which includes, but not limited to, fibronectin, collagen, laminin, keratin, fibrin, and fibrinogen.

The term "biological sample," as used herein, refers to adult or fetal mammalian body fluid containing cells with transdiferentiation or repair potential, which includes, but not limited to, serum, aspirates such as pleural fluid, cerebrospinal fluid, amniotic fluid, placental tissue and adipose tissue aspirates, peripheral blood, umbilical cord blood and bone marrow aspirates.

The term "biopolymer," as used herein, refers to synthetic polymers or polymers produced by living organisms, which includes, but not limited to, proteins, polypeptides and polysaccharides. Examples for polysaccharides include cellulose, starch, hyaluronic acid, heparin sulfate, chondroitin sulfate, and agarose.

The term "bone marrow aspirates," as used herein, refers to material pulled out the bone marrow cavity by suction, which includes, but is not limited to, BM Aspiration and BM biopsy.

The term "cell-adherent surface layer," as used herein, refers to surface treated to allow cell adherence, which includes, but is not limited to, corona treated bags or flasks.

The term "cell detachment solution," as used herein, refers to material used to prevent cell adherence to the surface, which includes, but is not limited to, Accutase, EDTA, EGTA, and Trypsin.

The term "cell phenotype," as used herein, refers to clusters of differentiation or CD markers expressed on the cell surface which includes, but is not limited to, CD14, CD34, CD38, CD44, CD45, CD73, CD90, CD105, CD166 and CD271.

The term "corona discharge," as used herein, refers to the well known treatment for polymeric surfaces that allows cell adherence, which includes, but is not limited to, corona treated bags, flasks or vessels for collecting adherent cells.

The term "conditions or disorders," as used herein, refers to a pathological change resulting in abnormal functions which includes, but is not limited to, tissue injuries, tissue degeneration, tissue atrophy, or tissue loss.

The term "growth medium," as used herein, refers to liquid material supplying nutrients required for cell growth, which includes, but is not limited to, X-vivo, RPMI-1640, DMEM, αMEM.

The term "incubating," as used herein, means mixing the components at a fixed temperature for a defined time period.

The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "plasma blood volume expander," as used herein, refers to liquids added to the blood to separate the components including red blood cells which include, but are not limited to, hydroxyethyl starch and gelatin polysuccinate.

The term "progenitor stem cells," as used herein, refers to cells with the ability to self-renew and to differentiate into other mature or less mature phenotypes which include, but are not limited to, multipotent mesenchymal stromal cells (MSC), adventitial reticular cells, vascular pericytes, fibroblasts and bone-lining cells.

The term "X-vivo," as used herein, refers to chemically defined media of non-animal origin, chemically defined, and optimized for use in human clinical trials, which include, but are limited to, X-vivo 10, X-vivo 15, and x-vivo 20.

The term "treat" or "treatment," as used herein, includes, but is not limited to, ameliorating a disease, lessening the severity of its complications, preventing it from manifesting, preventing it from recurring, merely preventing it from worsening, mitigating an undesirable biologic response (e.g., inflammation) included therein, or a therapeutic effort to effect any of the aforementioned, even if such therapeutic effort is ultimately unsuccessful.

DETAILED DESCRIPTION OF THE SYSTEM

Figure 1:
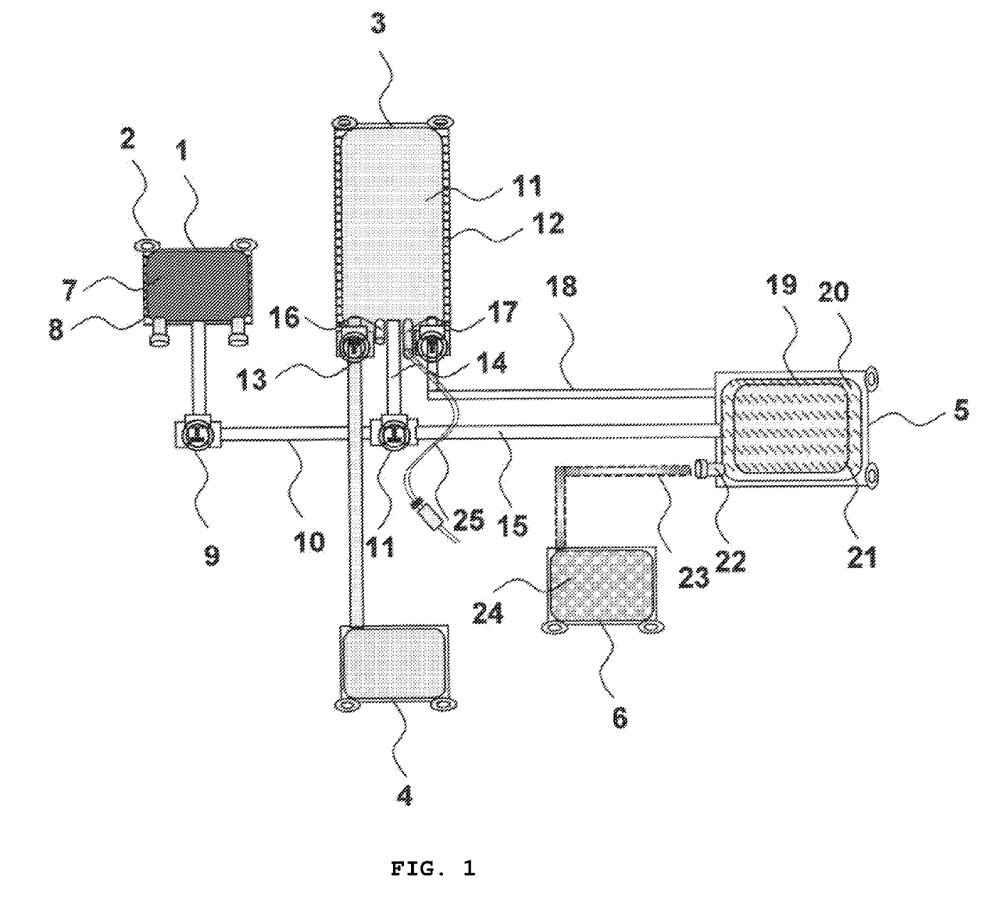
FIG. 1 is a side, cross-sectional view of a device embodying the stem cell isolation method of the present invention.

FIG. 1 shows a disposable set of bags comprising three bags 1, 3, and 4 with hanging rings 2, bar code labeling area, and contents free of any animal products. These bags are connected to the stem cell isolation bag (stem bag) 5 with tubing lines 10 through stopcocks 9, 11, 13, and 14. The stem bag 5 is corona-treated 19 to allow adherence of stem cells, and pre-coated with surface adherence materials 20 such as poly-L lysine for neural differentiation, laminin for epithelial differentiation, fibronectin for mesenchymal differentiation, etc., and contains X-Vivo medium (Cambrex) 21 suitable for human clinical trial. Bag 1 is graded 8 to allow fixed ratio mixing of hydroxyethyl starch (HES) 7 to the anticoagulated bone marrow or biological fluid sample 11 in bag 3 to reach a final HES concentration of 1.2%. The sample bag 3 has injection port 17 to introduce the bone marrow (BM) or biological fluid sample 25, a bacterial filtered air port 16, stopcock 13 to remove the sedimented red blood cells (RBCs) into bag 4, and stopcock 14 to allow plasma or centrifuged serum from the same sample to be collected through tubing 18 to the stem bag 5, avoiding the use of animal serum for adherent stem cell isolation. Bag 3 has anticoagulant 11 such as ACD, CPD, CPDA, heparin or sodium citrate. Optional bag 6 is connected to the stem bag by tubing 23 and contains preservative 24 such as dimethyl sulfoxide, glycerol, ethylene glycol or propylene glycol for long-term storage of adherent stem cells.

Figure 2:
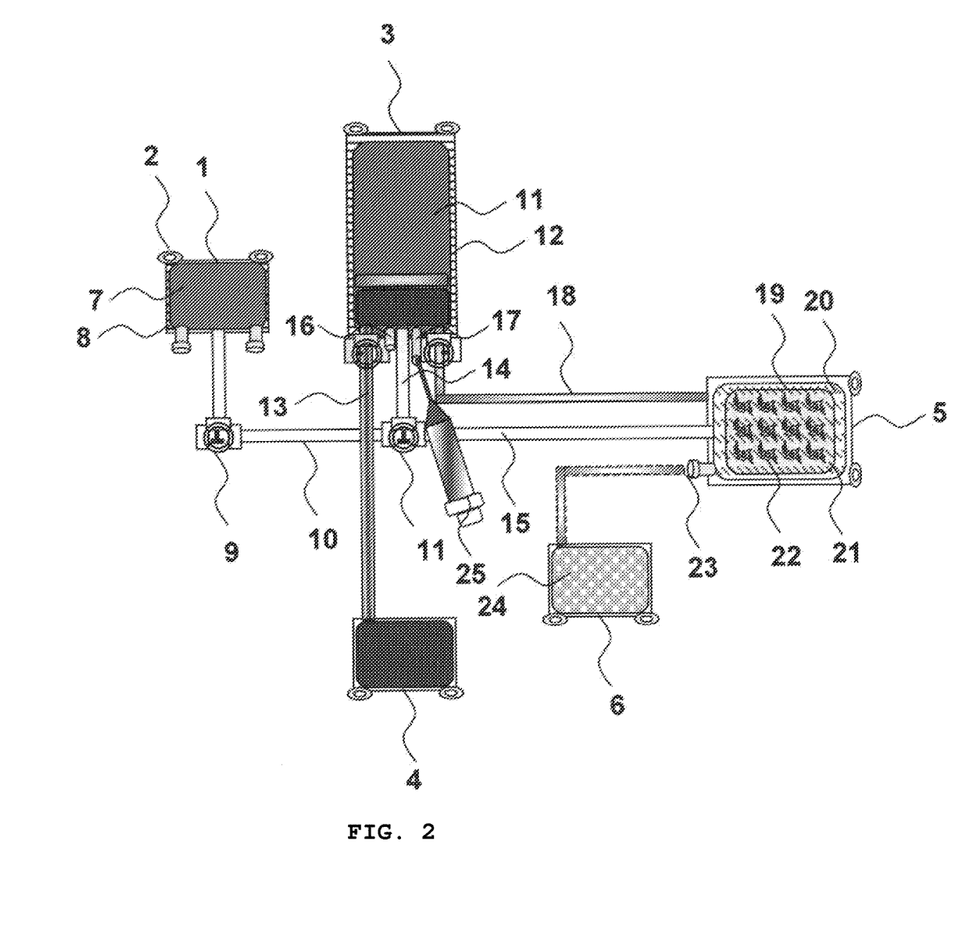
FIG. 2. is a side cross-sectional view of the embodiment of FIG. 1 in operation.

FIG. 2 shows a disposable set of bags comprising three bags 1, 3, and 4 with hanging rings 2, bar code labeling area, and contents free of any animal products. These bags are connected to the stem cell isolation bag 5 with tubing lines 10 through stopcocks 9, 11, 13, and 14. The stem bag 5 is corona-treated 19 to allow adherence of stem cells 22, pre-coated with surface adherence materials 20 such as poly-L lysine for neural differentiation, laminin for epithelial differentiation, fibronectin for mesenchymal differentiation, etc., and contains X-Vivo medium (Cambrex) 21 suitable for human clinical trial to separate adherent cells 22. Bag 1 is graded 8 to allow fixed ratio mixing of hydroxyethyl starch (HES) 7 to the anti-coagulated bone marrow or biological fluid sample 11 in bag 3 to reach a final HES concentration of 1.2%. The sample bag 3 has injection port 17 to introduce the BM or biological fluid sample 25, a bacterial filtered air port 16, stopcock 13 to remove the sedimented RBCs into bag 4, and stopcock 14 to allow plasma or centrifuged serum from the same sample to be collected through tubing 18 to the stem bag 5, avoiding the use of animal serum for stem cell isolation. Bag 3 has anticoagulant 11 such as ACD, CPD, CPDA, heparin or sodium citrate. Optional bag 6 connected to the stem bag by tubing 23 contains preservative 24 such as dimethyl sulfoxide, glycerol, ethylene glycol or propylene glycol for long-term storage of adherent stem cells.

Figure 3:
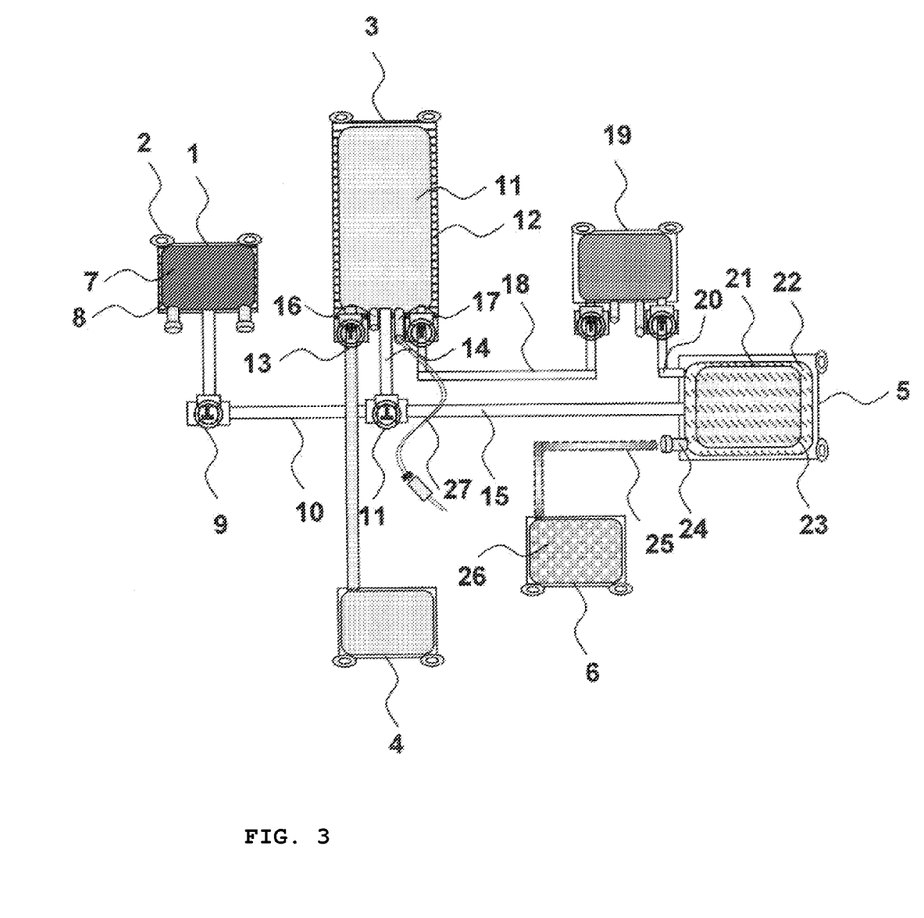
FIG. 3 is another side, cross-sectional view of a different device embodying the stem cell isolation method of the present invention.

FIG. 3 shows a disposable set of bags comprising four bags 1, 3, 4, and 19 with hanging rings 2, bar code labeling area and contents free of any animal products. These bags are connected to the stem cell isolation bag 5 with tubing lines 10 through stopcocks 9, 11, 13, and 14. The stem bag 5 is corona-treated 21 to allow adherence of stem cells and pre-coated with surface adherence materials 22 such as poly-L lysine for neural differentiation, laminin for epithelial differentiation, fibronectin for mesenchymal differentiation, etc., and contains X-Vivo medium (Cambrex) 23 suitable for human clinical trial. Bag 1 is graded 8 to allow fixed ratio mixing of hydroxyethyl starch (HES) 7 to anti-coagulated bone marrow or biological fluid sample 11 in bag 3 to reach a final HES concentration of 1.2%. Sample bag 3 has injection port 17 to introduce the BM or biological fluid sample 27, a bacterial filtered air port 16, stopcock 13 to remove the sedimented RBCs into bag 4, and stopcock 14 to allow plasma or centrifuged serum from the same sample to be collected through tubing 14 to the plasma collection bag 19 that is also connected through tubing 20 to the stem bag 5, avoiding the use of animal serum for stem cell isolation and allowing storage of plasma or serum for further cell culture. Bag 3 has anticoagulant 11 such as ACD, CPD, CPDA, heparin or sodium citrate. Optional bag 6 connected to the stem bag by tubing 25 contains preservative 26 such as dimethyl sulfoxide, glycerol, ethylene glycol or propylene glycol for long-term storage of adherent stem cells.

Figure 4:
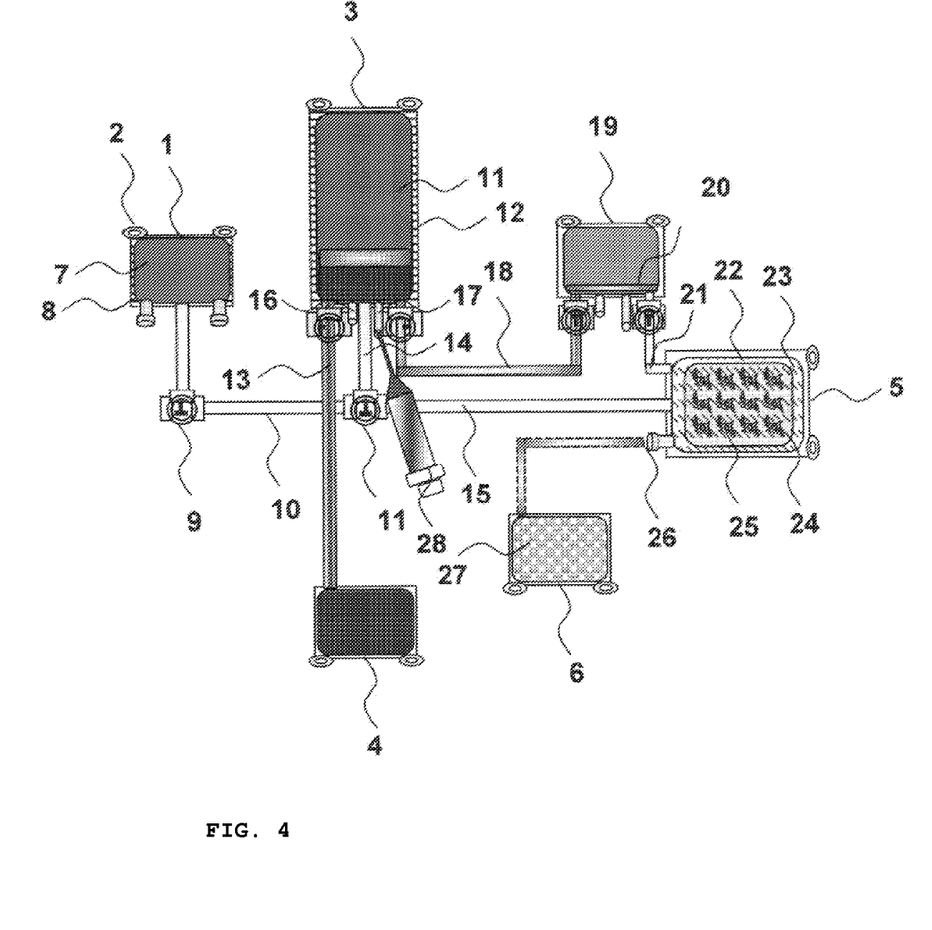
FIG. 4 is a side, cross-sectional view of the embodiment of FIG. 3 in operation.

FIG. 4 shows a disposable set of bags comprising four bags 1, 3, 4 and 19 with hanging rings 2, bar code labeling area, and contents free of any animal products. These bags are connected to the stem cell isolation bag 5 with tubing lines 10 through stopcocks 9, 11, 13 and 14. The stem bag 5 is corona-treated 22 to allow adherence of stem cells 25, and pre-coated with surface adherence materials 23 such as poly-L lysine for neural differentiation, laminin for epithelial differentiation, fibronectin for mesenchymal differentiation, etc., and contains X-Vivo medium (Cambrex) 24 suitable for human clinical trials to separate adherent cells 25. Bag 1 is graded 8 to allow fixed ratio mixing of hydroxyethyl starch (HES) 7 to the anti-coagulated bone marrow or biological fluid sample 11 in bag 3 to reach a final HES concentration of 1.2%. The sample bag 3 has injection port 17 to introduce the BM or biological fluid sample 28, and a bacterial filter air port 16, and stopcock 13 to remove the sedimented RBCs into bag 4 and stopcock 14 to allow plasma or centrifuged serum from the same sample to be collected through tubing 14 to the plasma collection bag 19 that allows further separation of the plasma rich stem cells layer 20, and is also connected through tubing 21 to the stem bag 5, avoiding the use of animal serum for stem cell isolation, and allowing storage of plasma or serum for further cell culture. Bag 3 has anticoagulant 11 such as ACD, CPD, CPDA, heparin or sodium citrate. Optional bag 6 connected to the stem bag by tubing 26 and contains preservative 27 such as dimethyl sulfoxide, glycerol, ethylene glycol or propylene glycol for long-term storage of adherent stem cells.

EXAMPLE

The present invention is described more fully by way of the following non-limiting example. Modifications of these examples will be apparent to those skilled in the art.

Human adherent bone marrow cells (ABMC) are isolated using bone marrow aspirates from the iliac crest of spinal cord injury patients. Cells are collected in blood collection bags with interiors coated with poly-L-lysine and containing a standard X-vivo medium and patients own serum or plasma. The cells are incubated for 3 days, and non-adherent cells are removed by replacing the medium with three washing steps. The adherent cells are lifted by incubation with Accutase at 37° C. for 5 min. Prior to transplantation of the isolated ABMC's, the samples are checked for cell phenotype, viability, and sterility. The present inventors surprisingly found that the cells separated from the bags were positive for CD90, CD105, CD166, and CD271, but had no expression of CD34, CD45, and CD14.

The stem cell-bag will be developed for use in a cell therapy strategy for treatment of Spinal Cord Injuries (SCI), in which autologous minimally manipulated ABMC's are transplanted by intrathecal injection. Spinal cord injury patients are treated with autologous ABMC therapy by intrathecal transplantation through lumbar puncture, receiving a cumulative target cell dose of between about $10^4$ and about $10^7$ bone marrow stem cells/kg, and the procedure is repeated monthly until the target dose is achieved. ABMC are suspended in 150 µl of saline solution are injected into the CSF by lumbar puncture.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A method for isolating and processing bone marrow derived stem cells comprising the steps of:
   (a) collecting a biological sample comprising adherent bone marrow stem cells;
   (b) transferring the biological sample to a first closed receptacle containing an anticoagulant;
   (c) adding to the first closed receptacle an amount of plasma blood volume expander effective to separate red blood cells from the biological sample;
   (d) transferring the biological sample from the first closed receptacle to a second closed receptacle through interconnected sterile tubing, the second closed receptacle having an interior surface coated with a cell-adherent surface-layer and containing a growth medium;
   (e) incubating the adherent bone marrow stem cells in said second closed receptacle for in between about two hours and about five days, wherein the adherent bone marrow stem cells adhere to the cell-adherent surface-layer, forming an adherent bone marrow stem cell layer;
   (f) washing the adherent bone marrow stem cell layer, wherein any non-adherent bone marrow stem cells are removed from the adherent bone marrow stem cell layer; and
   (g) collecting said adherent bone marrow stem cell layer to create collected bone marrow stem cells.

2. The method of claim 1, wherein said biological sample further comprises umbilical cord blood or bone marrow aspirates.

3. The method of claim 1, wherein said cell-adherent surface layer comprises a cell-adherent biopolymer, polypeptide, protein or polysaccharide.

4. The method of claim 3, wherein the interior surface of said second closed receptacle is corona discharge treated prior to coating with said cell-adherent surface layer.

5. The method of claim 3, wherein said cell-adherent surface layer comprises a coating of at least one basement membrane protein.

6. The method of claim 5, wherein said basement membrane protein is selected from the group consisting of fibronectin, collagen, laminin, keratin, fibrin, and fibrinogen.

7. The method of claim 3, wherein said cell-adherent surface layer comprises gelatin.

8. The method of claim 3, wherein said cell-adherent surface layer comprises at least one polysaccharide selected from the group consisting of hyaluronic acid, heparin sulfate, chondroitin sulfate, and agarose.

9. The method of claim 3, wherein said cell-adherent surface layer comprises poly-L-lysine or poly-D-lysine.

10. The method of claim 1, wherein step (f) further comprises replacing said growth medium at least once.

11. The method of claim 1, wherein step (g) comprises incubating said adherent bone marrow stem cell layer with a cell detachment solution.

12. The method of claim 1, further comprising the step of (h-1) of suspending said collected bone marrow stem cells in a pharmaceutically acceptable saline solution, wherein step (h-1) is performed after step (g).

13. The method of claim 1, further comprising the step of (h-2) of checking the collected bone marrow stem cells for at least of a cell phenotype, viability, and sterility, wherein step (h-2) is performed after step (g).

14. The method of claim 1, wherein the plasma blood volume expander is hydroxyethyl starch (HES) or gelatin polysuccinate.

* * * * *